US008377470B2

(12) United States Patent
Tanner et al.

(10) Patent No.: US 8,377,470 B2
(45) Date of Patent: Feb. 19, 2013

(54) NON-GELATIN SOFT CAPSULE SYSTEM

(75) Inventors: Keith E. Tanner, Safety Harbor, FL (US); Rickey S. Shelley, Largo, FL (US); Norman S. Stroud, Safety Harbor, FL (US); Elizabeth Youngblood, Valrico, FL (US)

(73) Assignee: R.P. Scherer Technologies, LLC, Carson City, NV (US)

( * ) Notice: Subject to any disclaimer, the term of this patent is extended or adjusted under 35 U.S.C. 154(b) by 0 days.

(21) Appl. No.: 13/543,244

(22) Filed: Jul. 6, 2012

(65) Prior Publication Data
US 2012/0269889 A1 Oct. 25, 2012

Related U.S. Application Data

(62) Division of application No. 10/984,205, filed on Nov. 8, 2004, now Pat. No. 8,231,896.

(51) Int. Cl.
*A61K 9/48* (2006.01)
(52) U.S. Cl. ........ 424/451; 424/452; 514/777; 514/778; 514/782
(58) Field of Classification Search ........................ None
See application file for complete search history.

(56) References Cited

U.S. PATENT DOCUMENTS

| | | | |
|---|---|---|---|
| 4,744,988 A | 5/1988 | Brox | |
| 4,780,316 A | 10/1988 | Brox | |
| 5,071,643 A | 12/1991 | Yu et al. | |
| 5,360,615 A | 11/1994 | Yu et al. | |
| 5,376,688 A | 12/1994 | Morton et al. | |
| 5,505,961 A | 4/1996 | Shelley et al. | |
| 5,735,105 A | 4/1998 | Stroud et al. | |
| 6,340,473 B1 | 1/2002 | Tanner et al. | |
| 6,387,400 B1 | 5/2002 | Tindal et al. | |
| 6,582,727 B2 | 6/2003 | Tanner et al. | |
| RE39,079 E | 4/2006 | Tanner et al. | |
| 2002/0081331 A1 | 6/2002 | Tanner et al. | |
| 2003/0085487 A1 | 5/2003 | Tanner et al. | |
| 2003/0104048 A1 | 6/2003 | Patel et al. | |
| 2004/0052839 A1 | 3/2004 | Archibald et al. | |
| 2005/0137262 A1 | 6/2005 | Hu et al. | |

FOREIGN PATENT DOCUMENTS

| | | |
|---|---|---|
| EP | 0086468 | 8/1983 |
| WO | 8802625 | 4/1988 |
| WO | 93/00891 | 1/1993 |
| WO | 9842294 | 10/1998 |
| WO | 0217855 | 3/2002 |
| WO | 2004024126 | 3/2004 |
| WO | 2005065665 | 7/2005 |

OTHER PUBLICATIONS

Anon., "General Carrageenan Application Technology," 1988, FMC Corporation, pp. 1-18.
Patel et al., "Advances in softgel formulation technology," 1989, Manufacturing Chemist, vol. 60, No. 7, pp. 26-28.
Patel et al., "Softgel Technology," 1989, Manufacturing Chemist, vol. 60, No. 8, pp. 47-49.
I. W. Kellaway, et al., "The Mechanical Properties of Gelatin Films," Parts I & II, Canadian Journal of Pharmaceutical Sciences, vol. 13, No. 4, pp. 83-90 (1978).
H. Seagar, "Soft Gelatin Capsules: A Solution to Many Tableting Problems," Pharmaceutical Technology, vol. 9, No. 9, pp. 84-104 (1985).
W.R. Ebert, "Soft Elastic Gelatin Capsules: A Unique Dosage Form," Pharmaceutical Technology, vol. 1, No. 5, pp. 44-50 (1977).
P. Johns et al., "Relationship between Collagen and Gelatin," The Science and Technology of Gelatin, Academic Press, Chapter 5 (1977).
V. Hostetler et al., "Capsules," The Theory and Practice of Industrial Pharmacy, Chapter 13, Lea & Febiger, Philadelphia (1970).
M.S. Patel et al., "Advances in Softgel Formulation Technology," Manufacturing Chemist, vol. 60, No. 7, pp. 26-28 (1989).

*Primary Examiner* — Robert A Wax
*Assistant Examiner* — Randeep Singh
(74) *Attorney, Agent, or Firm* — Fitzpatrick, Cella, Harper & Scinto

(57) ABSTRACT

A non-gelatin encapsulation system for liquid filled soft capsules, by nature of the carrier, the cationic-ionic balance of the carrier and the active ingredients, or the concentration of the active ingredients and excipients, are difficult or impossible to commercially encapsulate in gelatin capsules. In particular, the system is adapted for the encapsulation of highly basic, or alkaline, fills. The system provides for a predominantly starch and gelling carrageenan based shell, which displays high resistance to both concentrated fills and to alkaline fills, in particular, to those fills which contain the salt or salts of weak acids and strong bases.

7 Claims, No Drawings

NON-GELATIN SOFT CAPSULE SYSTEM

The present application is a divisional of U.S. Pat. application No. 10/984,205, filed Nov. 8, 2004, now U.S. Pat. No. 8,231,896 the entire disclosure of which is incorporated by reference herein.

TECHNICAL FIELD

The instant invention relates to a system for encapsulating certain materials that are traditionally difficult or impossible to encapsulate in gelatin capsules. More specifically, the invention is directed to a system for encapsulating highly basic liquid formulations in a non-gelatin soft capsule.

BACKGROUND OF THE INVENTION

Experience has long shown that pharmaceuticals or other items for human or animal consumption may be safely and conveniently packaged in a hard or soft gelatin (softgel) shell. Gelatin is a substantially pure protein food ingredient, obtained by the thermal denaturation of collagen, which is the most common structural material and most common protein in animals. Gelatin forms thermally reversible gels with water, and the gel melting temperature (<35° C.) is below that of human body temperature (37° C.), which gives gelatin products unique properties, such as reversible sol-gel transition states at near physiologic temperatures.

Gelatin is an amphoteric protein with an isoionic point between 5 and 9, depending on raw material and method of manufacture. Type A gelatin, with an isoionic point of 7 to 9, is derived from collagen with acid pretreatment. Type B gelatin, with an isoionic point of 4.8 to 5.2, is the result of alkaline pretreatment of the collagen. Like its parent protein collagen, gelatin is unique in that in contains, approximately, 16% proline, 26% glycine, and 18% nitrogen. Gelatin is not a complete protein food because the essential amino acid tryptophan is missing and the amino acid methionine is present only at a low level.

There are a large number of processes used in the manufacture of gelatin and the raw materials from which it is derived, which includes demineralized bone, pigskin, cowhide and fish. Gelatin can be derived from any edible material containing collagen. For reasons of economy, gelatin can be most practically be derived from collagen sources which would normally require refining before consumption or which would otherwise make up protein-containing waste material destined for animal feeds, agricultural fertilizers, or for other industries.

Gelatin capsules are traditionally divided into two general groups; hard shell gelatin capsules and soft gelatin capsules (softgels). In hard shell gelatin capsules, the capsule is in equilibrium with a relative humidity of less than 20%; they are formulated with a low ratio of dry plasticizer to dry gelatin (low amounts of plasticizer); and are traditionally made of two separately formed, cooperating, telescoping shells. On the other hand, softgels are most commonly in equilibrium with a relative humidity of between 20% and 30%, are formulated with a high ratio of dry plasticizer to dry gelatin (higher amounts of plasticizer); and are traditionally formed in a unitary process such as the rotary die encapsulation process described below.

Filled one-piece soft capsules or softgels have been widely known and used for many years and for a variety of purposes and are capable of retaining a liquid fill material. The fill material may vary from industrial adhesives to bath oils. More commonly, the softgels are used to enclose or contain consumable materials such as vitamins and pharmaceuticals in a liquid vehicle or carrier.

Encapsulation within a soft capsule of a solution or dispersion of a nutritional or pharmaceutical agent in a liquid carrier offers many advantages over other dosage forms, such as compressed, coated or uncoated solid tablets, or bulk liquid preparations. Encapsulation of a solution or dispersion permits accurate delivery of a unit dose, an advantage which becomes especially important when relatively small amounts of the active ingredient must be delivered, as in the case of certain hormones. Such uniformity is more difficult to achieve via a tableting process wherein solids must be uniformly mixed and compressed, or via incorporation of the total dose of active ingredient into a bulk liquid carrier which must be measured out prior to each oral administration.

Encapsulation of drugs in soft capsules further provides the potential to improve the bioavailability of pharmaceutical agents. Active ingredients are rapidly released in liquid form as soon as the shell ruptures. Complete disintegration of the capsule is not necessary for the active ingredients to become available for absorption, unlike the case of tableted compositions. Also, relatively insoluble active ingredients can be dispersed in a liquid carrier to provide faster absorption. A typical example involves a solution of a hydrophobic drug in a hydrophilic solvent. Upon ingestion, the shell ruptures in the stomach and the hydrophilic solution dissolves in the gastric juice. Acid soluble compounds remain in solution and are readily available for rapid absorption. Acid insoluble compounds may precipitate temporarily, in the form of a fine particle dispersion, but then redissolve quickly to give a solution with good bioavailability.

Soft capsules, most commonly, soft gelatin capsules, provide a dosage form which is readily accepted by patients, since the capsules are easy to swallow and need not be flavored in order to mask the unpleasant taste of the active agent. Soft capsules are also more easily transported by patients than bulk liquids, since only the required number of doses need be removed from the package.

Traditionally, both soft and hard-shell capsules have been manufactured using mammalian gelatin as the material of choice for producing the capsule envelope. The rotary die process developed by Robert Scherer in 1933 for producing one piece soft capsules utilizes the unique properties of gelatin to enable a continuous soft capsule manufacturing process. The inventive encapsulation system disclosed in this patent application is especially useful in the rotary die method of soft capsule manufacture.

Conventional manufacturing of soft capsules using the rotary die process utilizes mammalian gelatin in a process well known to those of skill in the art. Dry gelatin granules are combined with water and suitable plasticizers and the combination is then mixed and heated under vacuum to form a molten gelatin mass. The gelatin mass is held in its molten state while being formed or cast into films or ribbons on casting wheels or drums. The films or ribbons are fed under a wedge and between rotary encapsulation dies. Within the encapsulation dies, capsules are simultaneously formed, in pockets in the dies, from the films or ribbons, then filled, cut, and sealed. The seals are formed via a combination of pressure and heat as the capsule is filled and cut. Rotary die manufacture of soft gelatin capsules is disclosed in detail in The Theory and Practice of Industrial Pharmacy (Lachman, Lieberman and Kanig, Editors), 3rd Edition, published by Lea & Febiger. A good description of gelatin encapsulation techniques can also be found in WO 98/42294 (PCT/GB98/00830).

Gelatin formulations used to produce films suitable for making capsules within the rotary die process typically contain between 25% to 45% by weight mammalian gelatin. Levels below 25% by weight tend to lead to poor sealing of the capsule. The physical properties of the gelatin film are critical to the economic production of soft capsules. For example, the film must be strong enough to survive manipulation in the encapsulation machine, provide good sealing properties at temperatures below the melting point of the film, evidence rapid dissolution in gastric juices, and have sufficient elasticity to allow for the formation of the capsule.

There are, however, significant problems associated with gelatin capsules. In the case of gelatins derived from mammalian gelatin, there are concerns regarding the possible transmission of prions that are believed responsible for syndromes such as bovine spongiform encephalopathy (BSE or "mad cow" disease) and Jacob-Creutzfeldt Syndrome. There are also ethical, cultural, dietary, and religious restrictions in various parts of the world against products derived from certain animals. To answer concerns about the safety and consumer acceptability of mammalian gelatins, gelatins have been derived from fish sources, however, fish gelatins have particular fabrication requirements and are likely to become increasingly expensive with the depletion of the world's fish resources.

Regardless of the ultimate source of the gelatin from either mammal or fish sources, none of these approaches have answered what may be the most fundamental problem regarding gelatin encapsulation, namely, that not all substances and compounds may be successfully encapsulated, in a gelatin capsule.

Not all liquids are suitable as vehicles or carriers for the fill of a softgel. For example, water, propylene glycol, glycerin and low molecular alcohols, ketones, acids, amines and esters cannot be filled in softgels by themselves, or may only be present in small amounts. In particular, concentrations of water in the fill of greater than 20% by weight will dissolve the gelatin shell. Liquids that are suitable for filling softgels vary from water immiscible liquids such as vegetable oils, aromatic oils, aromatic and aliphatic hydrocarbons, chlorinated hydrocarbons, ethers and esters, to water miscible nonvolatile liquids. Examples of other acceptable carriers include polyethylene glycols and nonionic surfactants and other pharmaceutically acceptable solvent systems.

Even if the fill liquid is amenable to gelatin encapsulation, there are specified limitations to the use of certain fill vehicles for softgels. For example, the pH of the fill liquid should not be below 2.5 or above 7.5. At pH's below 2.5, the gelatin is hydrolyzed causing leaking, whereas at pH's greater than 7.5, the gelatin can also be hydrolyzed. Moreover, emulsions of oil/water or water/oil are not suitable for softgel encapsulation because the emulsions eventually break down, releasing water which dissolves the gelatin shell. The solvent or carrier in some cases must have sufficient solvating power to dissolve a large amount of the pharmaceutical agent to produce a highly concentrated solution, and yet not hydrolyze, dissolve, or discolor the gelatin shell.

Even when provided a suitable carrier and suitable agent for encapsulation, there can be problems in successful commercial encapsulation. One problem occurs with agents of low solubility that require a relatively large volume of solvent for solubilization, leading to the necessity for a large capsule. Often, it is not possible to dissolve the pharmaceutical agent in a volume of solvent small enough to produce a softgel that is appropriate from the standpoint of economics and patient acceptance.

Recently, various systems for increasing the solubility of low-solubility active ingredients have been described as, for example, in U.S. Pat. Nos. 5,071,643 and 5,360,615 to Yu, et al. These systems involve the titration of, as appropriate, acid or alkali into polyethylene glycol (PEG) containing a low-solubility pharmaceutical agent. In particular, the creation of a salt of a weak acid and strong alkali, such as potassium hydroxide or sodium hydroxide, markedly increases the solubility of the pharmaceutical agent in PEG. However, by converting a portion of the pharmaceutical agent to the salt of a weak acid and strong alkali and thereby increasing the solubility, hydroxide ion (—OH) is necessarily present as a reacting species and is available for degradation of the gelatin. This may occur by hydrolysis of the gelatin, a disruption of the ionic bonding between the gelatin helices, or by a combination of the two, along with other possible mechanisms. In fact, it is a long-established and widely held tenet of pharmaceutical chemistry that such salts cannot be encapsulated in gelatin capsules, unless they are highly diluted.

Thus, under the prior art, the pharmaceutical chemist is often faced with a true dilemma, desiring to use alkali to increase the solubility of a recalcitrant pharmaceutical agent in order to formulate a capsule small enough for commercial acceptance and/or to stabilize the drug substance; while at the same time being forced to restrict the use of alkali lest the capsule be impermissibly degraded.

Particular note must be taken of the need to formulate capsules that satisfy commercial, rather than theoretic, utility. While it may be possible to formulate certain basic fills in gelatin capsules as an initial matter of encapsulation, such formulations, as will be described below, are unable to satisfy the stability standards for commercial pharmaceutical products. Therefore, as will be seen below, it has, in the prior art, remained extremely difficult as a practical matter to encapsulate many basic substances in soft gelatin capsules.

A prototypical example of a pharmaceutical agent that has proven difficult to encapsulate in soft gelatin capsules is acetaminophen (APAP). Utilizing the enhanced solubility system described in U.S. Pat. Nos. 5,071,643 and 5,360,615 to Yu, et al.; Shelley et al. found, as taught in U.S. Pat. No. 5,505,961, that the sodium hydroxide or potassium hydroxide required to solubilize the acetaminophen at very high concentrations (those greater than about 27% by weight), increased the pH of the PEG solution to greater than 12, resulting in the degradation of the acetaminophen and the dissolving of the softgel shell.

By adding, inter alia, propylene glycol and polyvinylpyrrolidone, Shelley et al. were able to achieve concentrations of acetaminophen in a stable gelatin capsule preparation to 40% by weight, but not significantly more. Such an advance had the effect of obtaining the same size softgel for a 325 mg dose as for a 250 mg dose softgel product under the prior art. While significant, this still falls short of the desired dosage capabilities, which range even higher in the case of prescription formulated acetaminophen.

Such a problem in achieving suitable dosage systems wherein the active or actives must be formulated as a high concentration preparation is not restricted to acetaminophen, but also includes, by way of illustration and not limitation, such well-known drugs as ibuprofen, naproxen, pseudoephedrine hydrochloride, dextromethorphan hydrobromide, doxylamine succinate, guafenesin, diphenhydramine, aspirin, and caffeine; as well as certain dosage forms and concentrations of ranitidine, cimetidine, celecoxib, ritonavir, and fexofenadine; in addition to many others and combinations of the above enumerated drugs.

What has been needed, and heretofore unavailable, is a system for encapsulating those pharmaceutical agents and carriers that have heretofore proved refractory to encapsulation in gelatin capsules, due either to the effect of the concentration of the agent or carrier, or the basic nature of the fill. The present invention has solved this problem by a novel and unexpected use of a drug delivery system of a non-gelatin capsule shell resistant to alkali and, in one embodiment, a partially neutralized drug in which the provision of the salt of a weak acid and a strong alkali produced significantly high drug concentrations in acceptable quantities of solvent.

SUMMARY OF THE INVENTION

In its most general configuration, the present invention advances the state of the art with a variety of new capabilities and overcomes many of the shortcomings of the prior art soft capsules. In its most general sense, the present invention overcomes the shortcomings and limitations of the prior art in any of a number of generally effective compositions and methods.

The instant invention provides for a non-gelatin encapsulation system for certain difficult to encapsulate products, particularly, for those capsule fill formulas that, by nature of the carrier, the cationic-ionic balance of the carrier and the active ingredients, or the concentration of the active ingredients and excipients, are difficult or impossible to commercially encapsulate in gelatin capsules. The system provides for a predominantly starch and gelling carrageenan based capsule, which displays the novel and unexpected quality of high resistance to concentrated alkaline fills, in particular, to those fills which contain the salt or salts of weak acids and strong bases. The instant invention is particularly suitable for fills with a pH greater than about 7.5; more preferably fills with a pH greater than 8.0, and most preferably, for fills with a pH between 8.0 and 12.0.

Active ingredients that require high concentrations per dose, are inherently alkaline, or require formulation as a salt, include but are not limited to: ibuprofen, naproxen, acetaminophen, pseudoephedrine hydrochloride, dextromethorphan hydrobromide, doxylamine succinate, guafenesin, diphenhydramine, aspirin, caffeine, ranitidine, cimetidine, celecoxib, ritonavir, and fexofenadine, and combinations of these and other agents. The use of the system of the instant invention has allowed the successful manufacture of softgel dosage forms of concentrated solutions of ibuprofen, naproxen, and acetaminophen, containing larger dosages of the active ingredient of these compounds than has heretofore been possible in a commercially successful softgel of therapeutically reasonable size.

What is disclosed, therefore, is a soft capsule system for encapsulating chemical compounds, comprising a shell comprising a modified starch and a gelling carrageenan; and a fill, the fill including at least one active ingredient dissolved or dispersed in a carrier, wherein the fill has a pH greater than about 7.5. More preferably, the fill has a pH greater than about 8.0; and most preferably, the fill has a pH between about 8.0 and 12.0.

The shell of the system further comprises a mixture of starch, gelling carrageenan, water, a plasticizer and a buffer, wherein the starch and the gelling carrageen are at a weight to weight ratio of between at least 1.5 to 1 and 5.0 to 1. More preferably, the starch and the gelling carrageen are at a weight to weight ratio of between at least 2 to 1; and most preferably, the starch and the gelling carrageen are at a weight to weight ratio of at least 3 to 1.

The gelling carrageenan may comprise iota-carrageenan, kappa-carrageenan, and mixtures thereof. The starch is a modified starch selected from the group consisting of hydroxypropylated tapioca starch, hydroxypropylated maize starch, acid thinned hydroxypropylated corn starch, native potato starch, pregelatinized modified corn starches; and wherein said starch has a hydration temperature below about 90 degrees Centigrade.

The active agent may be ibuprofen and the ibuprofen may present in the capsule in a weight to weight ratio of at least 40%. The active agent may be acetaminophen, and the acetaminophen may be present in the capsule in a weight to weight ratio of at least 40%. The active agent may be naproxen, and the naproxen may be present in the capsule in a weight to weight ratio of at least 20%.

Furthermore, the fill may comprise an acidic active ingredient and an alkali agent sufficient to partially neutralize a portion of the active agent, by forming an equilibrium between the acidic active ingredient, and the salt of the acidic agent and alkali agent; and the degree of neutralization may also be between 40% and 100% of the acidic active ingredient.

By way of example and not limitation, the active agent or agents may also be selected from the group consisting of pseudoephedrine hydrochloride, dextromethorphan hydrobromide, doxylamine succinate, guafenesin, diphenhydramine, aspirin, caffeine, ranitidine, cimetidine, celecoxib, ritonavir, and fexofenadine and combinations thereof.

The system according to the invention can have alkali added to the fill formulation to enhance the stability and/or solubility of the active ingredient. In similar fashion, an acidic agent can be added to the fill, provided however. that the final pH of the fill formulation is above 7.5. This would be for highly basic active ingredients.

DETAILED DESCRIPTION OF THE INVENTION

The encapsulation system of the instant invention provides a significant advancement in the state of the art. The preferred embodiments of the inventive encapsulation system accomplish this by new and novel elements that demonstrate previously unavailable but preferred and desirable capabilities. The detailed description set forth below is intended merely as a description of the presently preferred embodiments of the invention, and is not intended to represent the only form in which the present invention may be constructed or utilized. The description sets forth the functions, means, and methods of implementing the invention in connection with the illustrated embodiments. It is to be understood, however, that the same or equivalent functions and features may be accomplished by different embodiments that are also intended to be encompassed within the spirit and scope of the claims.

Initial experimentation was prompted by the observation that a suspension of a proprietary acerola extract, representing a salt of a weak acid and a strong alkali, quickly degraded a sheet of gelatin capsule material made by the traditional art, while it appeared to have no effect on a sheet of non-gelatin encapsulation material made principally of starch and gelling carrageenan, according to the method of Tanner et al., as taught in U.S. Pat. Nos. 5,376,688 and 6,582,727 (incorporated herein in their entirety by reference). As would be understood by one skilled in the art, all reference in the following specification to and claims to starch refers to gelling starches, and all references to carrageenan refers to gelling carrageenans.

Initial Experimentation on the Effects of Alkali on Encapsulation Films

The observation that a formulation containing a basic extract of acerola did not appear to affect the non-gelatin film while quickly degrading a gelatin film prompted an examination of the effect of concentrated alkali on such films. While it is generally held that starch is itself susceptible to degradation by alkali, the results seen were an apparent paradox to this past belief, suggesting that additional mechanisms, and a mechanism hitherto undiscovered, were responsible for the observed resistance of the predominantly starch film to alkaline materials. Therefore, experimentation was undertaken to examine the effect of highly concentrated alkali on gelatin films, starch films, gelling carrageenan films, and the combined starch/gelling carrageenan film.

Films were cast by techniques well-known in the art with the compositions set forth in Table I.

TABLE I

Film Compositions for Testing with Concentrated Alkali

| Ingredient | Amount, % by weight |
|---|---|
| *Gelatin Film* | |
| Gelatin | 38 |
| Polysorb ® | 21 |
| Purified Water, USP | 41 |
| *Starch Film* | |
| Hydroxypropylated starch | 31 |
| Polysorb ® | 12.5 |
| Glycerol | 12.5 |
| di-Sodium Phosphate | 0.7 |
| Purified Water, USP | 43.3 |
| *Carrageenan Film* | |
| Iota-Carrageenan | 7.5 |
| Polysorb ® | 12.5 |
| Glycerol | 12.5 |
| di-Sodium Phosphate | 0.7 |
| Purified Water, USP | 66.8 |
| *Starch/Gelling Carrageenan Film* | |
| Hydroxypropylated starch | 23.5 |
| Iota-Carrageenan | 7.5 |
| Polysorb ® | 12.5 |
| Glycerol | 12.5 |
| di-Sodium Phosphate | 0.7 |
| Purified Water, USP | 43.3 |

The films were cast and allowed to form and set. A rectangular section of each film was cut, removed, and placed onto a wire test tube rack. Depressions were allowed to form in sections of each film. These depressions were then filled with concentrated alkali in the form of a pellet of potassium hydroxide. The test rig was then placed in and maintained in an oven at 30° C. and 95% relative humidity (RH.). Interaction between the alkali and the film was monitored at regular intervals.

Results:

In the gelatin film, the pockets were destroyed within two hours. The residue around the burned-through pockets was sticky or stringy in quality, indicative of breakdown of the gelatin.

In the starch film, there was no observed effect in the first four hours. At the five hour examination interval, the pockets were observed to exhibit sagging or dimpling, and had lost opacity, while the "control" area of the film remained semi-opaque. All pockets burned through within 24 hours of initiation of the experiment. The residues surrounding the burned-through pockets were discolored brown and were sticky or stringy, indicative of starch breakdown.

In the gelling carrageenan film, there was no observed effect after five hours. After 30 hours, the pockets remained intact with no destruction of structure observed.

In the starch/gelling carrageenan film, the film was regularly monitored for nine days. Throughout, and at the conclusion of the study, the pockets were found to be undamaged with no destruction of structure observed.

On the basis of this experiment, the following determinations can be made. Gelatin is rapidly degraded by strong alkali, while starch is also quickly degraded, but slightly less rapidly than gelatin. Carrageenan is unaffected by strong alkali, at least over the time span of this experiment. Surprisingly, and central to the instant invention, the starch/gelling carrageenan film was also unaffected by the strong alkali, even though the major component of the film, by a 3:1 ratio over the gelling carrageenan, was hydroxypropylated starch, which, as noted, is very susceptible to attack by alkali. The ratio of starch to carrageenan is found effective in a ratio of between 1.5 to 1 and 5 to 1, more preferably in a ratio of greater than 2:1, and most preferably in a ratio greater than 3:1. Furthermore, while the experimentation was conducted with iota-carrageenan, it is believed that similar results would be obtained with kappa-carrageenan and mixtures of iota- and kappa-carrageenan. The surprising conclusion is that there appears to be a synergistic relationship between starch and gelling carrageenan, that, when the two are combined into a film, serves to protect the starch of the film from degradation by alkali.

This experiment suggested the possibility that certain drug formulations, particularly those with alkaline properties, which had long been thought to be difficult or impossible to encapsulate, might, in a properly designed system, be amenable to stable and commercial production in a soft capsule.

EXAMPLE 1

Ibuprofen

Experimentation was undertaken regarding achieving commercially successful formulations of ibuprofen when the ibuprofen was concentrated above a level previously consistent with success in the prior art. At the onset, formulations were prepared to determine the concentration of ibuprofen above which it was not possible, from a commercial perspective, to prepare stable preparations in a traditional soft gelatin capsule.

Ibuprofen is 2-(4-isobutylphenyl)-propionic acid. It is a weak carboxylic acid that is traditionally administered in doses of 200 mg for over-the-counter (OTC) preparations, or 400 mg for prescription use. In order to achieve a solution in a suitable sized soft capsule that is chemically stable, formulators have developed a mixed ibuprofen and potassium ibuprofen solution in a polyethylene glycol solvent system, as taught in U.S. Pat. Nos. 5,071,643; 5,360,615; and 5,376,688. Typically, for this type of dosage form (softgel capsule), the dosage form must be chemically and physically stable for a period of not less than 6 months at 40° C. and 75% RH (relative humidity). If a product meets this quality specification, that is, it is chemically and physically stable under such accelerated testing for six months, it is highly predictive that the product will be stable for at least two years at normal shelf storage temperatures. On the other hand, if a product fails under such accelerated stability testing at the one month test interval, or any shorter time period; it will almost certainly exhibit the same failure at normal shelf storage temperatures.

Experimentation was undertaken to assess the effect of salt concentration, that is, to determine the relative susceptibility of gelatin and non-gelatin capsules to 100% neutralized potassium ibuprofen in polyethylene glycol 600 (PEG 600) at varying drug loading solutions, in an accelerated stability test protocol (40° C.-75% RH). Along with gelatin films made to standard formulations that are well-known in the art (i.e., films that are identical in composition to the films used to manufacture capsules using the rotary die encapsulation process) (Table II), non-gelatin starch/gelling carrageenan films were formed from the following compositions, as described in Table III.

TABLE II

Gelatin Capsule Film Formulation
(Wet-gel Gel Mass)

| Ingredient | Amount, % by weight |
|---|---|
| Gelatin | 38 |
| Polysorb ® | 21 |
| Purified water | 41 |
| TOTAL: | 100.00 |

Polysorb® is a sorbitol/sorbitan mixture that is used as a plasticizer and is made and distributed by Roquette, Inc. of France.

TABLE III

Non-Gelatin Starch/Gelling Carrageenan Capsule Shell Formulation
(Wet-gel Gel Mass)

| Ingredient | Amount, % by weight |
|---|---|
| Hydroxypropylated starch | 20-25 |
| Iota-Carrageenan | 6-8 |
| Plasticizer | 10-25 |
| Buffer | 0.5-1.0 |
| Purified water | qs (as suffices) |
| TOTAL: | 100.00 |

For the purpose of the study, failure was defined as breakage or liquefaction of the test area of the film, on visual inspection. Sets of 4 tests for each film and testing agent was conducted. Failure occurred when one or more of the 4 films failed. Intact means that none of the 4 films failed. The results are set forth in Table IV.

TABLE IV

Gelatin Film Compatibility Testing of 100% Neutralized
Potassium Ibuprofen
Accelerated Stability Testing; 40° C.-75% RH

| Drug Loading in Solution (% by weight) | 24 Hours | 48 Hours | 120 Hours | 216 Hours |
|---|---|---|---|---|
| 25 | Intact | Intact | Intact | 2/4 Failed |
| 30 | Intact | 1/4 Failed | All Failed | All Failed |
| 35 | Intact | 1/4 Failed | All Failed | All Failed |
| 40 | Intact | 1/4 Failed | All Failed | All Failed |
| 45 | 1/4 Failed | 1/4 Failed | All Failed | All Failed |
| 50 | 1/4 Failed | 2/4 Failed | All Failed | All Failed |

This study showed that even at relatively lower levels of drug loading in solution, i.e., at 25% and 30% by weight, in a short but intensive stress study, which is generally accepted as being highly predictive of extended storage results, there were significant failures with the gelatin film. This strongly suggests that even at such low loading levels, gelatin encapsulation was unlikely to be suitable for this type of product.

In line with the observation that non-gelatin films appeared to be more resistant to basic solutions, the experiment was repeated, using the same drug concentrations and testing parameters, exposing the ibuprofen formulations to films prepared using the starch/gelling carrageenan composition set out above. The results were are set forth in Table V.

TABLE V

Non-Gelatin Film Compatibility Testing of 100% Neutralized
Potassium Ibuprofen
Accelerated Stability Testing; 40° C.-75% RH

| Drug Loading in Solution (% by weight) | 24 Hours | 48 Hours | 120 Hours | 216 Hours |
|---|---|---|---|---|
| 25 | All Intact | All Intact | All Intact | All Intact |
| 30 | All Intact | All Intact | All Intact | All Intact |
| 35 | All Intact | All Intact | All Intact | All Intact |
| 40 | All Intact | All Intact | All Intact | All Intact |
| 45 | All Intact | All Intact | All Intact | All Intact |
| 50 | All Intact | All Intact | All Intact | All Intact |

These results indicated that the starch/gelling carrageenan film is much more suitable, even for surprisingly high concentrations of potassium ibuprofen, than the gelatin film. In a companion study, similar films were tested with partially and fully neutralized Ibuprofen/Potassium Ibuprofen, to evaluate the behavior of these films.

TABLE VI

Gelatin Film Compatibility Testing of Partially to Fully
Neutralized Ibuprofen/Potassium Ibuprofen
Accelerated Stability Testing; 40° C.-75% RH

| Degree of Neutralization (%) | 24 Hours | 48 Hours | 120 Hours | 216 Hours |
|---|---|---|---|---|
| 20 | Intact | Intact | Intact | Intact |
| 40 | Intact | Intact | Intact | Intact |
| 60 | Intact | Intact | Intact | 2/4 Failed |
| 80 | Intact | Intact | 2/4 Failed | All Failed |
| 100 | Intact | Intact | 3/4 Failed | 3/4 Failed |

The study confirmed that while these compounds could be initially encapsulated in gelatin capsules, within a very short time period, while on accelerated stability testing, a significant failure rate ensued at relatively higher neutralization levels.

In line with the observation that non-gelatin capsules appeared to more resistant to basic solutions, the experiment was repeated, using the same degrees of neutralization and testing parameters, using a non-gelatin, starch/gelling carrageenan film. The results are set forth in Table VII.

TABLE VII

Non-Gelatin Film Compatibility Testing of Partially to Fully
Neutralized Ibuprofen/Potassium Ibuprofen;
Accelerated Stability Testing; 40° C.-75% RH

| Degree of Neutralization (%) | 24 Hours | 48 Hours | 120 Hours | 216 Hours |
|---|---|---|---|---|
| 20 | Intact | Intact | Intact | Intact |
| 40 | Intact | Intact | Intact | Intact |
| 60 | Intact | Intact | Intact | Intact |
| 80 | Intact | Intact | Intact | Intact |
| 100 | Intact | Intact | Intact | Intact |

Next, experimentation was undertaken to assess the effect of partial neutralization, that is, to determine the relative susceptibility of gelatin and non-gelatin capsules to varying levels of ibuprofen/potassium ibuprofen, partially to fully neutralized with potassium hydroxide in polyethylene glycol 600 (PEG 600) at 40% by weight drug loading solutions, on an accelerated stability test protocol (40° C.-75% RH). Capsules were prepared containing 200 mg of ibuprofen as a solution of the drug in polyethylene glycol (PEG) 600. For the purpose of the study, failure was defined as leakage, rupture, or liquefaction of the capsule on visual inspection, and a stable rating was given in the absence of the same. The results are set forth in Table VIII.

TABLE VIII

Gelatin and Non-Gelatin Encapsulation of Partially Neutralized Ibuprofen/Potassium Ibuprofen; Accelerated Stability Testing; 40° C.-75% RH

| Degree of Neutralization (%) | Shell Type (Polymer) | Stability Result at One Month |
|---|---|---|
| 40 | Gelatin | Stable |
| 60 | Gelatin | Failed (Liquefied) |
| 80 | Gelatin | Failed (Liquefied) |
| 40 | Starch/Gelling Carrageenan | Stable |
| 60 | Starch/Gelling Carrageenan | Stable |
| 80 | Starch/Gelling Carrageenan | Stable |

The starch/carrageenan capsules containing the highly neutralized fill formulations were further examined at a 3 month and 6 month storage interval. The capsules were found to be physically stable and unaffected by the fill material.

In view of the complete failure of the gelatin capsules containing the highly neutralized formulations after only a modest period of accelerated stability testing, capsules were prepared both with gelatin and starch/gelling carrageenan shells and were examined after extremely brief testing periods, to determine the conditions under which gelatin capsules are unstable when filled with the ibuprofen formulations.

TABLE IX

Gelatin and Non-Gelatin Encapsulation of Partially Neutralized Ibuprofen/Potassium Ibuprofen Accelerated Stability Testing; 40° C.-75% RH

| Degree of Neutralization (%) | Shell Type (Polymer) | Time on storage, days, and test result | | |
|---|---|---|---|---|
| | | 5 | 10 | 15 |
| 60 | Gelatin | Failed (Leaking) | Failed (Leaking) | Failed (Liquefied) |
| 80 | Gelatin | Failed (Some liquefaction) | Failed (Liquefied) | Failed (Liquefied) |
| 60 | Starch/Carrageenan | Stable | Stable | Stable |
| 80 | Starch/Carrageenan | Stable | Stable | Stable |

Given the unexpected and surprising superiority of the starch/gelling carrageenan capsule for encapsulating this product under accelerated stability testing, it was decided to further test the gelatin and non-gelatin capsule formulations under less stressful testing parameters, namely, 30° C.-60% RH; and 25° C.-60% RH. The results are set forth in Tables X through XIII.

TABLE X

Gelatin Encapsulation of Partially Neutralized Ibuprofen/Potassium Ibuprofen; 30° C.-60% RH Stability Testing

| Degree of Neutralization (%) | 90 Days |
|---|---|
| 40 | Stable |
| 60 | Failed (Liquefied) |
| 80 | Failed (Liquefied) |

TABLE XI

Non-Gelatin Encapsulation of Partially Neutralized Ibuprofen/Potassium Ibuprofen; 30° C.-60% RH

| Degree of Neutralization (%) | 90 Days |
|---|---|
| 40 | Stable |
| 60 | Stable |
| 80 | Stable |

The starch/carrageenan capsules containing the highly neutralized fill formulations were further examined at a 6 month and 12 month storage interval. The capsules were found to be physically stable and unaffected by the fill material.

TABLE XII

Gelatin Encapsulation of Partially Neutralized Ibuprofen/Potassium Ibuprofen; 25° C.-60% RH

| Degree of Neutralization (%) | 180 Days | 270 Days |
|---|---|---|
| 40 | Stable | Stable |
| 60 | Stable | Failed (Leaking) |
| 80 | Failed (Liquefied) | Failed (Liquefied) |

TABLE XIII

Non-Gelatin Encapsulation of Partially Neutralized Ibuprofen/Potassium Ibuprofen; 25° C.-60% RH

| Degree of Neutralization (%) | 180 Days | 270 Days |
|---|---|---|
| 40 | Stable | Stable |
| 60 | Stable | Stable |
| 80 | Stable | Stable |

The starch/carrageenan capsules containing the highly neutralized fill formulations were further examined at a 12 month and 18 month storage interval. The capsules were found to be physically stable and unaffected by the fill material.

From this data it can be concluded that the encapsulation system of the instant invention can create a soft ibuprofen capsule, that was stable under commercial conditions, and that could contain an increased concentration of ibuprofen.

EXAMPLE 2

Naproxen

From the results above, it was hypothesized that the surprising results obtained with the starch/gelling carrageenan encapsulation of partially neutralized and concentrated solutions of ibuprofen/potassium ibuprofen could be extended to other, similarly hard to solubilize active ingredients.

Naproxen is (S)-6-methoxy-α-methyl-2-naphthaleneacetic acid. It is a weak acid. It is typically administered as tablets or capsules of the naproxen sodium salt at a dose of 220 mg, which is approximately equivalent to 200 mg of the free acid form of naproxen.

Previous attempts to encapsulate a solution of highly concentrated naproxen sodium in soft gelatin capsules had been unsuccessful. During storage, the drug substance degrades the gelatin in the capsule shell and the capsule leaks. Even minor leaks are devastating from a commercial perspective, as a single leaking capsule will contaminate an entire package and render them useless. In order to study the stability of a typical solution formulation of naproxen sodium, the fill formulation set forth in Table XIV was developed.

TABLE XIV

Naproxen Sodium Fill Formulation

| Ingredient | Mg/Softgel | Amount, % by weight |
|---|---|---|
| Naproxen sodium | 200.00 | 24.0 |
| Purified water | 73.6 | 8.0 |
| Polyethylene glycol (PEG) | 623.4 | 68.0 |
| TOTAL: | 917.00 | 100.00 |

The naproxen sodium fill formulation was encapsulated using a gelatin-free, starch/gelling carrageenan composition with ingredients and amounts set forth in Table III.

To compare the behavior of the non-gelatin starch/gelling carrageenan capsule shell formulation with that of standard gelatin based capsules, softgel capsules were made in preparation for stability testing using the starch/gelling carrageenan gel mass formulation shown above in Table III and the typical gelatin based gel mass shell traditionally used for this type of fill formulation, shown above in Table II. The capsules were placed on accelerated stability testing (40° C.-75% RH) with the results being set forth in Table XV.

TABLE XV

Naproxen Sodium Formulation Encapsulated in Traditional Gelatin and Inventive Non-Gelatin Capsules Accelerated Stability Testing 40° C.-75% RH

| Shell Type (Polymer) | Stability Result-One Month | Stability Result-Six Months |
|---|---|---|
| Gelatin | Failed (Liquefied) | Not tested |
| Starch/Gelling Carrageenan | Stable | Stable |

Visual observation of the non-gelatin starch/gelling carrageenan shells at the six month stability testing time showed that they were unaffected by the fill composition.

EXAMPLE 3

Acetaminophen

Acetaminophen is N-acetyl-p-aminophenol. It is typically administered as tablets or capsules at does in the range of 250 mg to 500 mg, alone or in combination with other drug substances. In order to study the stability of a typical highly concentrated solution formulation of acetaminophen (500 mg of drug substance) the fill formulation set forth in Table XVI was developed.

TABLE XVI

Fill Formulation of Acetaminophen

| Ingredient | Mg/Softgel | Amount, % by weight |
|---|---|---|
| Acetaminophen | 500.00 | 42.66 |
| Potassium Acetate | 130.00 | 11.09 |
| Potassium Hydroxide | 44.0 | 3.75 |
| Polyvinyl pyrrolidone (PVP) | 23.0 | 1.96 |
| Purified water | 91.0 | 7.78 |
| Polyethylene glycol (PEG) | 384.00 | 32.76 |
| TOTAL: | 1,172.00 | 100.0 |

The acetaminophen fill formulation was diluted into a dilute aqueous formulation for pH measurement and was found to have a pH of approximately 12; making the formulation, therefore, highly basic. The fill formulation was encapsulated in the non-gelatin, starch/gelling carrageenan formula shell according to Table I, along with a second lot of gelatin capsules of traditional formulation, according to Table II, and then subjected to accelerated testing and comparison as reported above for naproxen sodium.

TABLE XVII

Acetaminophen Formulation Encapsulated in Traditional Gelatin, and Non-Gelatin Capsules According to the Instant Invention; Accelerated Stability Testing 40° C.-75% RH

| Shell Type (Polymer) | Stability Result-One Month | Stability Result-Six Months |
|---|---|---|
| Gelatin | Failed (Liquefied) | Not tested |
| Starch/Gelling Carrageenan | Stable | Stable |

Therefore, by utilizing the encapsulation system of the instant invention, it has become possible for the first time to produce softgel capsules containing 500 mg of acetaminophen in a capsule that is within the normally acceptable parameters of capsule size (slightly in excess of 1 gram).

EXAMPLE 4

Comparison of Gelatin and Non-Gelatin Film Stabilities Using Concentrated Salt Formulations In an attempt to further investigate the observed resistance of the starch/gelling carrageenan film to concentrated basic or alkaline salts, experiments were conducted using films cast from the starch/gelling carrageenan and gelatin gel mass formulations set forth in Example 3. The films were formed and spread over a holding device such that small depressions could be formed in the surface of the film. A depression was formed and subsequently filled with the concentrated suspension of the salt formulation. Simultaneously, two acidic solutions were tested by the same protocol. The compatibility test rig was then placed into an oven maintained at 40° C. and 75% RH, and left under open exposure conditions to accelerate the reaction between the salt, or acid, and film substrate. This is well-known in the art to be an extremely aggressive mode of stability testing, resulting in acceleration in the interaction between shell and fill of over 260 times normal rates. It was anticipated that the films would be examined at daily intervals for evidence of deformation or deterioration; however, as detailed below, the surprising and very rapid deterioration of the gelatin mass film halted the experiment at an early stage.

The following basic salts, salts of weak acid with a strong alkali, and weak acids, were tested according to the protocol above and the results are set forth in Table XVIII.

TABLE XVIII

Comparison of Gelatin and Non-Gelatin Film Stabilities Using Concentrated Salt Formulations

| Compound | Film Type and Test Result After 24 Hours at 40° C.-75% RH | |
|---|---|---|
|  | Starch/Gelling Carrageenan | Gelatin |
| Acerola (Basic Extract) | Pass | Fail |
| Ammonium acetate | Pass | Fail |
| Potassium acetate | Pass | Fail |
| Potassium citrate | Pass | Fail |
| Potassium Hydrogen Phthalate | Pass | Fail |
| Potassium $PO_4$-(dibasic) | Pass | Fail |
| Sodium $PO_4$-(tribasic) | Pass | Fail |
| Citric acid | Fail | Fail |
| Tartaric acid | Fail | Fail |

In summary, the overall results of the compatibility and stability studies clearly show that the novel encapsulation system of the instant invention is resistant to alkaline/basic drug substances and formulations, and can be used for the development of softgel products that are not feasible using traditional gelatin-based shell formulations.

Industrial Applicability

The encapsulation system of the instant invention provides a soft capsule system having a shell made principally of a starch/gelling carrageenan; and a carrier for capsule fill in which at least one active agent is dissolved or dispersed, said fill having a pH greater than 7.5. This innovative system allows the successful encapsulation of a wide range of products previously found unsuitable for encapsulation in traditional gelatin capsules.

We claim:

1. A non-gelatin soft capsule system for encapsulating chemical compounds, said non-gelatin soft capsule system comprising:
   a shell comprising a modified starch or a native potato starch and a gelling carrageenan, wherein the weight to weight ratio of starch to gelling carrageenan is between 1.5 to 1 and 5 to 1; and
   a fill, said fill comprising:
   at least one active ingredient dissolved or dispersed in at least one carrier,
   wherein the fill has a pH greater than 7.5,
   wherein the shell exhibits resistance to degradation caused by alkaline fills,
   wherein said shell further comprises water, a plasticizer and a buffer, and
   wherein said gelling carrageenan comprises kappa-carrageenan.

2. A non-gelatin soft capsule system for encapsulating chemical compounds, said non-gelatin soft capsule system comprising:
   a shell comprising a modified starch or a native potato starch and a gelling carrageenan, wherein the weight to weight ratio of starch to gelling carrageenan is between 1.5 to 1 and 5 to 1; and
   a fill, said fill comprising:
   at least one active ingredient dissolved or dispersed in at least one carrier,
   wherein the fill has a pH greater than 7.5,
   wherein the shell exhibits resistance to degradation caused by alkaline fills,
   wherein said shell further comprises water, a plasticizer and a buffer, and
   wherein said gelling carrageenan comprises a mixture of iota-carrageenan and kappa-carrageenan.

3. A non-gelatin soft capsule system for encapsulating chemical compounds, said non-gelatin soft capsule system comprising:
   a shell comprising a modified starch or a native potato starch and a gelling carrageenan, wherein the weight to weight ratio of starch to gelling carrageenan is between 1.5 to 1 and 5 to 1; and
   a fill, said fill comprising:
   acetaminophen dissolved or dispersed in at least one carrier, and
   an alkali agent sufficient to partially neutralize a portion of said acetaminophen by forming an equilibrium between (1) said acetaminophen and (2) the salt of said acetaminophen and said alkali agent,
   wherein the fill has a pH greater than 7.5, and
   wherein the shell exhibits resistance to degradation caused by alkaline fills.

4. The non-gelatin soft capsule system according to claim 3, wherein said acetaminophen is present in the non-gelatin soft capsule system in a weight to weight ratio of at least 40%.

5. A non-gelatin soft capsule system for encapsulating chemical compounds, said non-gelatin soft capsule system comprising:
   a shell comprising a modified starch or a native potato starch and a gelling carrageenan, wherein the weight to weight ratio of starch to gelling carrageenan is between 1.5 to 1 and 5 to 1; and
   a fill, said fill comprising:
   naproxen dissolved or dispersed in at least one carrier, and
   an alkali agent sufficient to partially neutralize a portion of said naproxen by forming an equilibrium between (1) said naproxen and (2) the salt of said naproxen and said alkali agent,
   wherein the fill has a pH greater than 7.5, and
   wherein the shell exhibits resistance to degradation caused by alkaline fills.

6. The non-gelatin soft capsule system according to claim 5, wherein said naproxen is present in the non-gelatin soft capsule system in a weight to weight ratio of at least 20%.

7. A non-gelatin soft capsule system for encapsulating chemical compounds, said non-gelatin soft capsule system comprising:
   a shell comprising a modified starch or a native potato starch and a gelling carrageenan, wherein the weight to weight ratio of starch to gelling carrageenan is between 1.5 to 1 and 5 to 1; and
   a fill, said fill comprising:
   at least one active ingredient dissolved or dispersed in at least one carrier,
   wherein the fill has a pH greater than 7.5, and
   wherein the shell exhibits resistance to degradation caused by alkaline fills,
   wherein said at least one active ingredient is selected from the group consisting of pseudoephedrine hydrochloride, dextromethorphan hydrobromide, doxylamine succinate, guaifenesin, diphenhydramine, aspirin, caffeine, ranitidine, cimetidine, celecoxib, ritonavir, fexofenadine, and combinations thereof.

* * * * *